US007919447B1

(12) United States Patent
Klinkhammer et al.

(10) Patent No.: US 7,919,447 B1
(45) Date of Patent: Apr. 5, 2011

(54) ARRAY OF SELF-ADHESIVE CLEANING PRODUCTS

(75) Inventors: Michael E. Klinkhammer, Racine, WI (US); Russell B. Wortley, Kenosha, WI (US); Michelle C. Dauchy, Racine, WI (US)

(73) Assignee: S.C. Johnson, Inc, Racine, WI (US)

( * ) Notice: Subject to any disclaimer, the term of this patent is extended or adjusted under 35 U.S.C. 154(b) by 0 days.

(21) Appl. No.: 12/850,553

(22) Filed: Aug. 4, 2010

Related U.S. Application Data

(63) Continuation-in-part of application No. 12/723,216, filed on Mar. 12, 2010.

(51) Int. Cl.
*C11D 17/00* (2006.01)
*C11D 3/386* (2006.01)
*C11D 3/48* (2006.01)
*C11D 7/42* (2006.01)
*A61L 11/00* (2006.01)

(52) U.S. Cl. ........ 510/191; 510/192; 510/195; 510/221; 510/238; 510/336; 510/370; 510/383; 510/392; 510/396; 510/403; 510/438; 510/440; 510/445; 510/446; 510/447; 424/76.1; 424/76.7

(58) Field of Classification Search .................. 510/191, 510/192, 195, 221, 238, 336, 370, 383, 392, 510/396, 403, 438, 440, 445, 446, 447; 40/1, 40/308, 310, 312; 424/76.1, 76.7
See application file for complete search history.

(56) References Cited

U.S. PATENT DOCUMENTS

| | | | | |
|---|---|---|---|---|
| 3,790,048 | A | 2/1974 | Luciano et al. | |
| 4,413,760 | A | 11/1983 | Paton | |
| 4,955,747 | A | 9/1990 | Tarver | |
| 5,020,693 | A | 6/1991 | Ernst et al. | |
| 5,242,057 | A | 9/1993 | Cook et al. | |
| 5,284,263 | A | 2/1994 | Papciak | |
| 5,377,853 | A | 1/1995 | Papciak | |
| 5,421,663 | A | 6/1995 | Bravo | |
| 5,443,161 | A | 8/1995 | Jonese | |
| 5,485,919 | A | 1/1996 | Samberg et al. | |
| 5,588,560 | A | 12/1996 | Benedict et al. | |
| 5,636,933 | A | 6/1997 | Vizsolyi | |
| 5,715,841 | A | 2/1998 | Utecht | |
| 5,732,716 | A | 3/1998 | Utecht | |
| 5,944,237 | A | 8/1999 | Gouldson | |
| 6,024,094 | A | 2/2000 | Utecht | |
| 6,159,181 | A | 12/2000 | Crossman et al. | |
| 6,168,022 | B1 | 1/2001 | Ward et al. | |
| 6,357,945 | B1 | 3/2002 | Losier et al. | |
| 6,454,095 | B1 | 9/2002 | Brisebois et al. | |
| 6,491,165 | B2 | 12/2002 | Kuske et al. | |
| 6,568,530 | B2 | 5/2003 | Takahashi et al. | |
| 6,601,705 | B2 | 8/2003 | Molina et al. | |
| 6,615,688 | B2 | 9/2003 | Wessel | |
| 6,667,286 | B1 * | 12/2003 | Dettinger et al. | ............. 510/191 |

(Continued)

FOREIGN PATENT DOCUMENTS

| | | | |
|---|---|---|---|
| JP | 2007106817 | A | 4/2007 |

(Continued)

*Primary Examiner* — Lorna M Douyon
(74) *Attorney, Agent, or Firm* — Ronald E. Andermann

(57) ABSTRACT

An array of self-adhesive cleaning products, the array having a first self-adhesive cleaning product, the product being a gel, and a second self-adhesive cleaning product, the second product being a solid.

11 Claims, 3 Drawing Sheets

U.S. PATENT DOCUMENTS

| | | | |
|---|---|---|---|
| D484,755 S | 1/2004 | Shonfeld et al. | |
| 6,701,828 B1 | 3/2004 | Burns et al. | |
| 6,752,293 B2 | 6/2004 | So | |
| 6,910,823 B2 | 6/2005 | Policicchio et al. | |
| 6,992,053 B2 * | 1/2006 | Cermenati et al. | 510/238 |
| 7,084,203 B2 | 8/2006 | Shibahara et al. | |
| 7,144,173 B2 | 12/2006 | Policicchio et al. | |
| D537,344 S | 2/2007 | O'Brien et al. | |
| D537,722 S | 3/2007 | Jaichandra et al. | |
| D538,164 S | 3/2007 | Zach et al. | |
| D539,147 S | 3/2007 | O'Brien | |
| 7,226,231 B2 | 6/2007 | Py et al. | |
| 7,520,406 B2 | 4/2009 | Jaichandra et al. | |
| D592,513 S | 5/2009 | Zach et al. | |
| D592,527 S | 5/2009 | Serio et al. | |
| D596,033 S | 7/2009 | Zach et al. | |
| 7,709,433 B2 | 5/2010 | Veltman et al. | |
| 2002/0148742 A1 | 10/2002 | Bisbal et al. | |
| 2003/0136704 A1 | 7/2003 | Burgess | |
| 2005/0277568 A1 | 12/2005 | Keenan et al. | |
| 2005/0279579 A1 | 12/2005 | Milk et al. | |
| 2006/0034905 A1 | 2/2006 | Singh et al. | |
| 2006/0167419 A1 | 7/2006 | Fiechter et al. | |
| 2006/0234886 A1 | 10/2006 | Massaro et al. | |
| 2007/0241016 A1 | 10/2007 | Piczon | |
| 2008/0058239 A1 | 3/2008 | Evers et al. | |
| 2008/0098630 A1 | 5/2008 | Frankenbach et al. | |
| 2008/0099041 A1 | 5/2008 | Evers et al. | |
| 2008/0119607 A1 | 5/2008 | Shibahara et al. | |
| 2008/0190457 A1 * | 8/2008 | Veltman et al. | 134/22.19 |
| 2008/0247805 A1 | 10/2008 | deVirag et al. | |
| 2008/0255017 A1 * | 10/2008 | Dettinger et al. | 510/191 |
| 2009/0215661 A1 | 8/2009 | Klinkhammer et al. | |
| 2009/0215909 A1 | 8/2009 | Wortley et al. | |
| 2009/0325839 A1 | 12/2009 | Wortley et al. | |
| 2010/0050344 A1 * | 3/2010 | Peltz et al. | 8/137 |
| 2010/0093586 A1 | 4/2010 | Klinkhammer et al. | |
| 2010/0120648 A1 | 5/2010 | Veltman et al. | |
| 2010/0130399 A1 | 5/2010 | Abbas et al. | |
| 2011/0002871 A1 * | 1/2011 | Leipold | 424/76.1 |

FOREIGN PATENT DOCUMENTS

| | | | | |
|---|---|---|---|---|
| WO | 99/38788 | | | 5/1999 |
| WO | WO 99/66017 | A1 | * | 12/1999 |
| WO | WO 02/26925 | A1 | * | 4/2002 |
| WO | 2007008531 | | | 1/2007 |
| WO | 2008058853 | A1 | | 5/2008 |
| WO | WO 2008/125451 | A1 | * | 10/2008 |
| WO | WO 2009/106220 | A1 | * | 9/2009 |
| WO | 2009/155115 | A3 | | 3/2010 |

* cited by examiner

ARRAY OF SELF-ADHESIVE CLEANING PRODUCTS

CROSS REFERENCE TO RELATED APPLICATIONS

This application is a continuation application that claims the benefit of U.S. Non-Provisional patent application Ser. No. 12/723,216 filed Mar. 12, 2010, which is incorporated in its entirety herein by this reference and is a continuation-in-part application which claims the benefit of U.S. Non-Provisional patent application Ser. No. 12/388,588 filed Feb. 19, 2009, which is also incorporated in its entirety herein by this reference.

TECHNICAL FIELD

In some embodiments, the present disclosure is directed to an array of self-adhering compositions for toilet care, or other home cleaning applications.

BACKGROUND OF THE DISCLOSURE

Self-adhesive compositions which dissipate after a certain number of uses (i.e., exposure to ambient conditions, water, and the like) are designed to provide users with an easy-to-use, and versatile option for approaching any number of cleaning tasks.

The design of the self-adhesive composition typically affects function, performance, and cost. For example, one self-adhesive composition may be used to provide a residual cleaning effect, as opposed to a different composition which may be used to provide an economical solution to a user.

Many merchandising systems may provide for guidance on items based on an individual item's function. For example, the Scrubbing Bubbles® Fresh Brush product (S.C. Johnson & Son, Inc., Racine, Wis.) is marketed with a specific user and function in mind. Due to the particularity in which the item functions (i.e., there is only one use for the item), there is no need to specify differences to the consumer. Some products of the identical type, albeit with minor physical differences, to perform the same general function. For example, the Charmin® toilet paper brand (The Procter & Gamble Co., Cincinnati, Ohio) provides "Ultra Soft" and "Ultra Strong" products. The two products are both toilet paper products, which perform the same function, but are positioned as being the ideal for different consumers. Specifically, Charmin® advertising calls out that one product is directed to a consumer that prefers a soft, cushy product whereas another product is directed to a consumer that prefers a stronger, more resilient product. The two products are differentiated on-shelf primarily by color. A consumer who does not pay attention to the labeling may accidentally purchase the strong product instead of the soft product, but will still be able to achieve the same end function. This is not the case for products with different intended functions.

There is, unfortunately, no way to provide a one design fits all approach due to the specificity regarding cost and function that many formulas provide. This is especially true in cleaning products, such as bath care and/or toilet care products. For instance, a consumer who seeks a relatively high level of convenience and a relatively long-lasting or particularly aggressive product may not be interested in a lower-cost single-use product which provides a high level of fragrance. Clearly, it is difficult, if not impossible, to design a single product configuration which will appeal to every consumer in the market for toilet, or other, cleaning products.

Thus, there exists the need for a variety of self-adhesive cleaning products that provides a variety of products which corresponds to the different user's income level, intended use, and preferred mode of application, among other things.

SUMMARY OF THE INVENTION

In a first nonlimiting embodiment, an array of self-adhesive cleaning products may include: (1) a first self-adhesive cleaning product; and (2) a second self-adhesive cleaning product having a surface area that includes a first portion capable of adhering to a hard surface; and a second portion capable of supporting the first self-adhesive cleaning product.

In a second nonlimiting embodiment, an array of self-adhesive cleaning products may include: (1) a first self-adhesive cleaning product, the first cleaning product providing a benefit selected from the group consisting of: detersive, cleansing, fragrancing, disinfecting, septic, corrosive, enzymatic, and the like; and (2) a second self-adhesive cleaning product, the second cleaning product having a surface area and providing a benefit selected from the group consisting of: detersive, cleansing, fragrancing, disinfecting, septic, corrosive, enzymatic, and the like; wherein a first portion of the surface area is capable of adhering to a hard surface; and a second portion of the surface area is capable of supporting the first self-adhesive cleaning product; and wherein the benefit provided by the first cleaning product is different from the benefit provided by the second product.

BRIEF DESCRIPTION OF THE DRAWINGS

The following detailed description of specific nonlimiting embodiments of the present disclosure can be best understood when read in conjunction with the following drawings, where like structures are indicated with like reference numerals and in which.

DETAILED DESCRIPTION

Definitions

Figure 1:
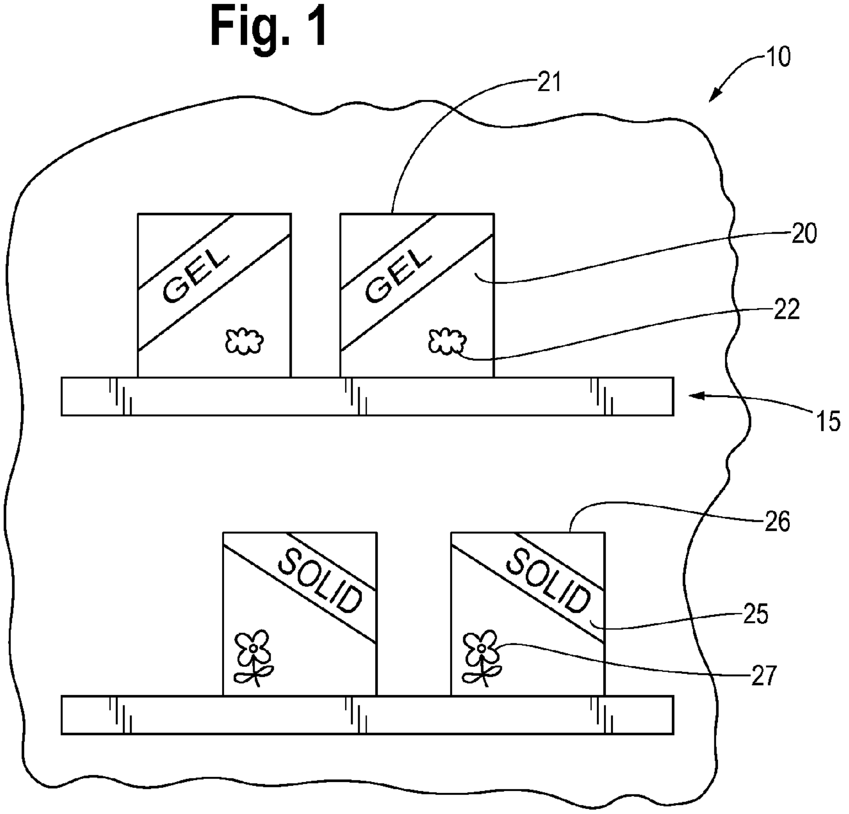
FIG. 1 shows a front view of an exemplary retail shelf unit having products displayed on the shelf unit.

As used herein, "self-adhesive product" refers to any gel, paste, wax, solid, or the like that may be adhered to, or otherwise provide a self-support from, a surface. By self-support, it is meant that a product will not require any additional device, or other mechanical means, to maintain and/or support and/or otherwise suspend the product in a fixed place. In some embodiments, there may be gravitational forces acting against the product. For example, a product may be intended to be adhered to the side of a toilet bowl underneath the rim. In some embodiments, the surface is a ceramic surface, such as a toilet bowl or a sink. In other nonlimiting embodiments, a surface may be glass, metal, plastic, stone, and the like. In some embodiments, self-adhesive product expressly does not include a separate layer of glue. It is thought that many glues which may be used to provide a means for attachment to a surface will leave an unwanted residue behind on the surface. In some other embodiments, self-adhesive product may be washed away from the surface on which it is adhered without leaving a residue on the surface. In other embodiments, the composition of the product may be substantially uniform throughout. In one embodiment, a product may be washed away from a surface after being subject to one or more flushes.

In a particular embodiment, a self-adhesive product may comprise one or more surfactants. In other embodiments, a self-adhesive product is not required to be placed into a mechanical support unit. In other embodiments still, a self-adhesive product may be a toilet care product. An exemplary self-adhesive product that may be used for toilet care applications is the Scrubbing Bubbles® Toilet Gel product that is available from S.C. Johnson & Son, Inc. (Racine, Wis.). An exemplary mechanical support unit is described in U.S. Des. Pat. No. D423,639. A mechanical support unit may be distinguished from an applicator and/or application device ("device") because, in some embodiments, the product that is being dispensed and/or that is delivering any beneficial effect must be located within, or otherwise used in conjunction with, the support device as it is providing and/or delivering product and/or its beneficial effect.

Self-Adhesive Product: Adhesion and Use Characteristics

In a simplified exemplary embodiment, a self-adhesive product may be any product which may be affixed to a non-horizontal surface, such as the inner surface of a toilet bowl, in a first configuration without the use of a mechanical device and which may be substantially maintained in the first configuration despite exposure to an incidental force, such as from water from a flush.

In one embodiment, a self-adhesive product may be described as any product that, upon being subjected to the "Flush Resiliency Test" described herein, adheres to the surface of the toilet bowl for at least about 5 flushes. In another embodiment, a self-adhesive product adheres to the surface of the toilet bowl for more than at least about 100 flushes. In still another embodiment, a self-adhesive product adheres to the surface of the toilet bowl for more than about 500 flushes. In yet another embodiment, a self-adhesive product adheres to the surface of the toilet bowl for from about 5 flushes to about 1000 flushes. In a different embodiment still, a self-adhesive product adheres to the surface of the toilet bowl for from about 100 flushes to about 1000 flushes. In another embodiment, a self-adhesive product adheres to the surface of the toilet bowl for from about 100 flushes to about 500 flushes.

Regarding the amount of self-adhesive product that may be released or otherwise expended, in some embodiments a self-adhesive product may be one in which there is a loss of from about 0.5% to about 2% of the initial product weight per flush, according to the Flush Resiliency Test.

One of skill in the art may appreciate that the product may have an initial size, shape, weight, density, and have any product distribution, that is suitable for the intended purpose. In one nonlimiting embodiment, the self-adhesive product may have an initial weight of from about 2 g to about 15 g. In another nonlimiting embodiment, the product may have an initial weight of from about 5 g to about 10 g. In some embodiments, the self-adhesive product may have a shape selected from the group of: symmetrical, asymmetrical, round, square, star, heart, triangle, domed, circular, oblong, rectangular, octagonal, hexagonal, pentagonal, the like, and combinations thereof.

Self-Adhesive Product: Product Presentation

A self-adhesive product may be provided in any product form or state that is suitable for the intended application. In some embodiments, a self-adhesive product may be a solid. In solid form, the self-adhesive product may be the result of an extrusion. The product may be malleable. The product may be forcibly adhered to a surface. The product may have a hardness of from about 50 to about 150 tenths of a millimeter according the "Hardness Test" as described herein. An exemplary self-adhesive product in solid form is described in U.S. Pat. Pub. No. US 2008-0190457.

In other embodiments, a self-adhesive product may be a gel. The gel may be formed by a hot melt process. The gel may have a melt temperature of from about 50oC to about 80oC. The gel may have a viscosity of from about 150,000 cps to about 400,000 cps as measured by a cone and plate viscometer. In some embodiments, a self-adhesive gel product may be able to be self-adhered to both wet and dry surfaces. An exemplary self-adhesive product in gel form is described in U.S. Pat. Pub. No. US 2009-0325839.

Product Presentation: Surface Spreading

As described supra, the disclosed compositions provide the unexpected benefit over existing compositions of, inter alia, increased mobility and transport. Exemplary compositions are made according to the Detailed Description and are tested for surface spreading using the "Surface Spreading Test" described below.

Surprisingly, it is noticed that the addition of the surfactants provide a significant increase in transport of the compositions. In one embodiment, the compositions provide a transport rate factor of less than 55 seconds. In another embodiment, the compositions provide a transport rate factor of less than about 50 seconds. In still another embodiment, the compositions provide a transport rate factor of from about 0 seconds to about 55 seconds. In another embodiment, the compositions provide a transport rate factor of from about 30 seconds to about 55 seconds. In yet still another embodiment, the compositions provide a transport rate factor of from about 30 seconds to about 50 seconds. In still another embodiment, the compositions provide a transport rate factor of from about 30 seconds to about 40 seconds.

Product Presentation: Adhesion

In some embodiments, the products disclosed herein may adhere to a solid surface under relatively harsh conditions. It is surprisingly discovered that it may be advantageous for the product to be able to adhere to a surface for a period of at least 5 hours, as measured by the "Adhesion Test" described below. In one embodiment, a product has a minimum adhesion of greater than about 8 hours. In another embodiment, a product has a minimum adhesion of from about 8 hours to about 70 hours.

As used herein, "brand" or "branded" refers to any relatively well-known identifier which at least some consumers will recognize as trustworthy and/or of providing a high level of performance and/or with some sort of particular functionality. In some embodiments, "brand" refers to an identifier that is known nationally. In other embodiments, "brand" refers to an identifier that is known globally, or within large regional areas. In other embodiments still, "brand" refers to a bathroom cleaner identifier, such as Scrubbing Bubbles® (S.C. Johnson & Son, Racine, Wis.), Toilet Duck®(S.C. Johnson & Son, Racine, Wis.), Mr. Clean (The Procter & Gamble Co., Cincinnati, Ohio), and the like.

As used herein, "indicia" refers to one or more identifying markings, which may include words and/or graphics and/or other symbols describing how a product may be used. In one embodiment an indicia may describe how a product is to operate during use.

As used herein, "array" refers to a series of two or more products which, in some embodiments, may be marketed under a common brand name on a store shelf, or otherwise within a proximity of each other that a consumer can visually identify the two or more products from the retail aisle. While it is commonplace to have commonly branded products on the same store shelves, it is not common to provide a shelf space which provides products which may be used complimentarily or in unison. Further, there is no such product(s) which are self-adhesive and used for cleaning purposes.

As used herein, "cleaning product" and or product for "cleaning purposes" refers to a product which may be marketed as being able to provide a benefit which may be selected from the group consisting of: detersive, cleansing, fragrancing, disinfecting, septic, corrosive, enzymatic, the like, and combinations thereof.

Composition

As described herein, an exemplary self-adhesive product may be in, but not limited to, a gel format or a solid format. Nonlimiting examples of a self-adhesive gel cleaning product is the Scrubbing Bubbles® Toilet Gel product (S.C. Johnson & Son, Inc., Racine, Wis.) and a nonlimiting example of a self-adhesive solid cleaning product is the Toilet Duck® Stick-On Strip product (S.C. Johnson & Son, Inc., Racine, Wis.).

Array

In some embodiments, an array of self-adhesive compositions may comprise a series of products which correspond to different users' intended tasks and price point.

One of skill in the art typically recognizes that a product may be identified to consumers with a written description of the product's intended function on the packaging itself. For example, "toilet bowl cleaner", "daily shower cleaner", etc. Such description is often expressed by some combination of words or phrases. In some embodiments, the consumer's choosing process is further simplified by providing one or more indicia on the label and/or packaging that indicates a use. In another nonlimiting embodiment, a means for describing a home cleaning product by providing one or more visual cues or indicia which may communicate a particular message to a consumer may be provided.

For example, FIG. 1 provides an example of an array 10 on a retail shelf unit 15, the array 10 comprising a first product 20 and a second product 25 is provided. In the exemplary embodiment, the first product 20 comprises a gel product that has a general purpose of delivering surfactant to the inner surface of a toilet bowl. The on-shelf packaging 21 wherein the first product 20 is stored has a first indicium 22 on the on-shelf packaging 21 which provides an indication that the first product provides benefits of providing a cleaning effect. For example, the first indicium 22 may be of suds, or a bar of soap, or the like. The second product 25 comprises a paste that has a general purpose of providing a fragrance to the toilet bowl. The on-shelf packaging 26 wherein the second product 25 is stored has a second indicium 27 on the on-shelf packaging 26 which provides an indication that the second product provides a fragrance. For example, the second indicium 27 may be of a flower, perfume bottle, or the like. In some embodiments, the on-shelf packaging of the first product 20 is substantially similar to the on-shelf packaging of the second product 25 with the exception of the indicia 22, 27.

Figure 2:
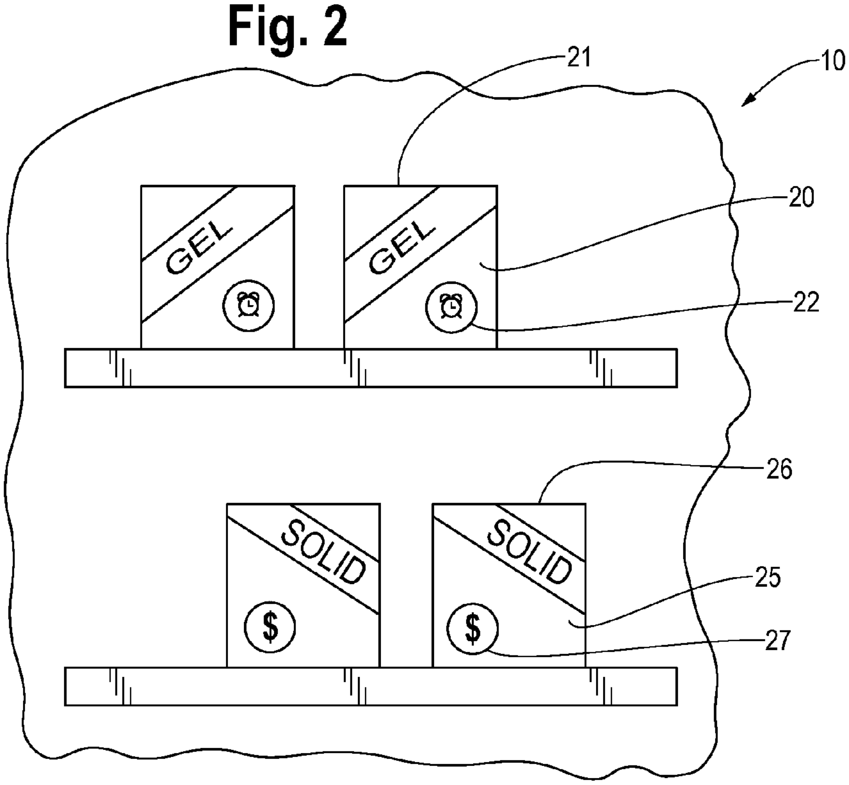
FIG. 2 shows a front view of an exemplary retail shelf unit having products displayed on the shelf unit.

Another nonlimiting example may be described by FIG. 2. In the embodiment shown in FIG. 2, there may be an array 10 comprising a first product 20 and a second product 25. In the exemplary embodiment, the first product 20 comprises a gel that has a general purpose of providing a cleaning benefit to a toilet bowl. The first product 20 also provides a relatively long-lasting cleaning benefit. The on-shelf packaging 21 wherein the first product 20 is stored has an indicium 22 on the on-shelf packaging 21 which provides an indication that the first product is long lasting. For example, the first indicium 22 may be of a clock, calendar, or the like. Alternatively, the first indicium 22 may be of suds, or a bar of soap, or the like.

The second product 25 comprises a solid that has a general purpose of providing a cleaning benefit to a toilet bowl. The second product 25 is relatively economical compared to the first product 20 due to a less-involved dispensing system, fewer doses, and the like. The on-shelf packaging 26 wherein the second product 25 is stored has an indicium 27 on the on-shelf packaging 26 which provides an indication that the second product is economical. For example, the second indicium 27 may be of a dollar sign, or the like. Alternatively, the second indicium 27 may be of suds, or a bar of soap, or the like.

The array of self-adhesive articles and marketing platform described herein may also be applied to fields other than home cleaning. For example, self-adhesive compositions may be used in drain care, pest control, auto care, and the like. In the nonlimiting embodiment described herein, the array of self-adhesive articles relates to an assortment of self-adhesive cleaning products wherein each product includes properties and/or characteristics wherein such properties and/or characteristics are observable from a functional, cost and/or purpose-of-use standpoint.

In some embodiments, the properties may include distribution of surfactant(s) (i.e., cleaning), fragrancing, deodorizing, disinfecting, and the like. In other embodiments, the self-adhesive products may be distinguished by number of uses (i.e., duration), number of doses included, and the like. In other embodiments still, the products may be distinguished by dispensing means, dosing size, and the like.

In one embodiment an array may include a first self-adhesive cleaning product and a second self-adhesive cleaning product. In the described embodiment, the first self-adhesive cleaning product may be applied to a surface via an applicator device, and the second self-adhesive cleaning product may be applied to a surface by hand. One of skill in the art will appreciate that the inclusion of an applicator in a product will generally increase the cost. Thus, in order to provide an array of products to consumers at different price points.

As mentioned above, for each of the uses described herein, there may be a distinct product for such a use. One of skill in the art will appreciate that there may be a certain degree of overlap between products. For example, a first self-adhesive cleaning product may be a paste and provide a cleansing benefit, while a second self-adhesive cleaning product may be a gel and also provide a cleansing benefit. The difference between the first product and the second product in the array is that the products are provided in different forms, which may allow the manufacturer with the ability to provide consumers with a variety of price points.

Figure 3A:
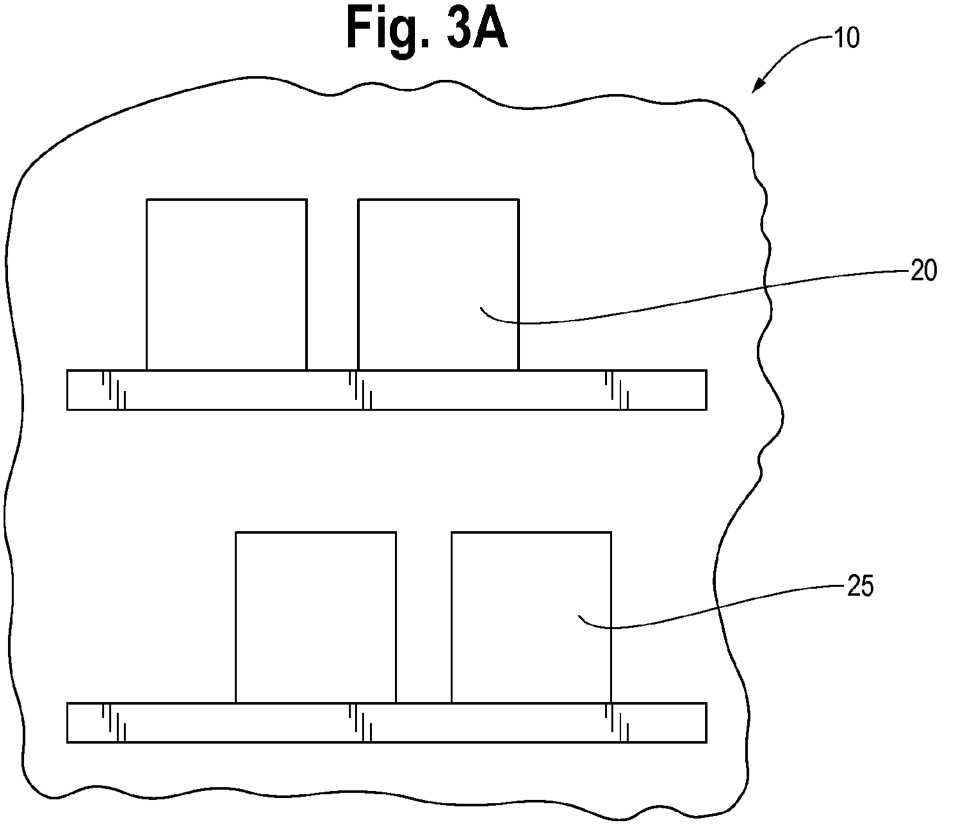
FIG. 3A shows a front view of an exemplary retail shelf unit having products displayed on the shelf unit.
Figure 3B:
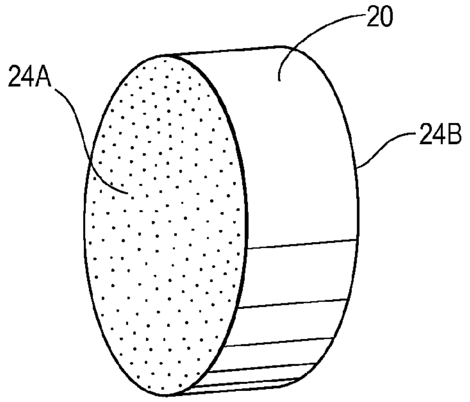
FIG. 3B shows a perspective view of a nonlimiting example of a product which may be used in an array.
Figure 3C:
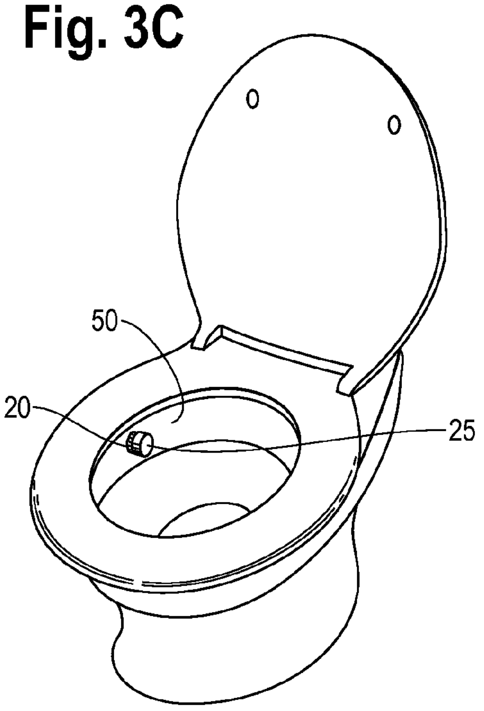
FIG. 3C shows a perspective view of a nonlimiting example of a product which may be used in an array as the product may be used in a consumer's toilet.

In an embodiment described by FIG. 3A, there is an array 10 comprising a first product 20 and a second product 25. In the embodiment shown in FIG. 3B, the first product 20 is self adhesive, and the first product may be provided such that there is a first adhesive portion 24A, wherein the first adhesive portion 24A may be capable of adhering to the inner surface of a toilet bowl (50, FIG. 3C) or other hard surface (not shown). The first product 20 may be provided such that there is a second adhesive portion 24B, wherein the second adhesive portion 24B may then adhere a separate product, such as the second product (25, FIG. 3A) to provide an "anchored" system between the first and second products (FIG. 3C). An exemplary self-adhesive portion may be exemplified in WO 2009/106220A1. It is thought that such an array may be particularly beneficial because this allows for a manufacturer to provide consumers with a wide variety of products that may suit the individual consumer's needs.

In one embodiment, the first product 20 may have an adhesion to the hard surface of at least about 5 hours. In another embodiment, the first product may have an adhesion to the hard surface of from about 8 hours to about 70 hours. In another embodiment still, the first product 20 may adhere to the second product 25 for at least the same length of time as the first product 20 adheres to the hard surface.

Pick-and-Choose

Figure 4:
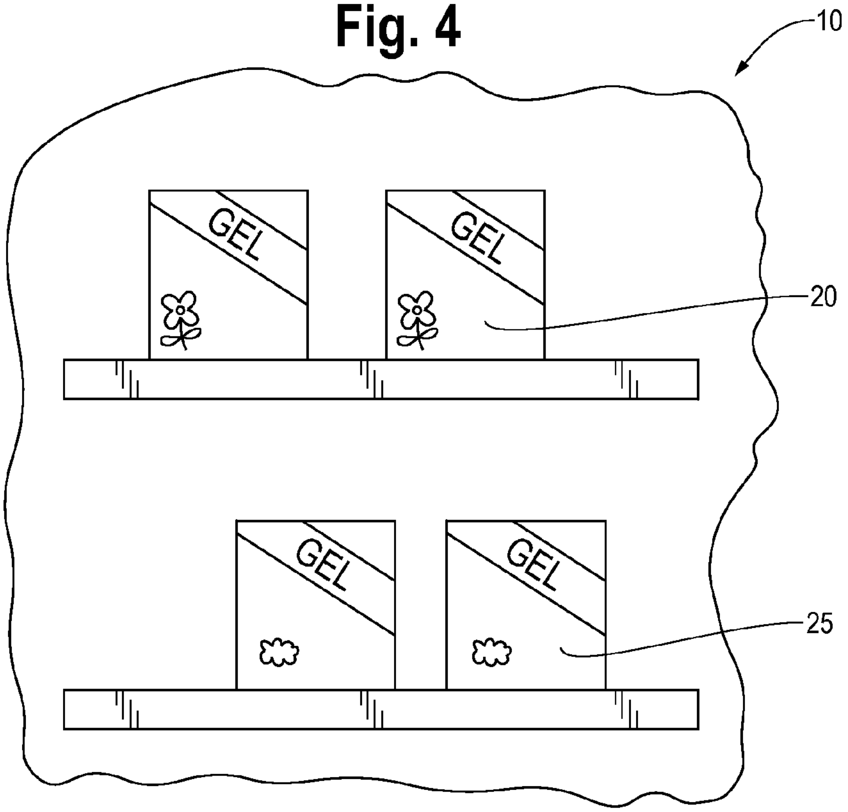
FIG. 4 shows a front view of an exemplary retail shelf unit having products displayed on the shelf unit.

In another embodiment shown in FIG. 4, the array 10 of products provides a user the option to customize her use experience by combining one or more products having different functions together. For example, the array may comprise a first product 20 and a second product 25. The first product 20 and second product 25 may be provided to the consumer in substantially the same shape and physical form, but may provide different compositions and/or active ingredients.

For example, the first product 20 may provide a cleaning benefit. The second product 25 may provide a fragrancing benefit. Additional and/or alternative products and/or benefits may be selected from the group consisting of: detersive, cleansing, fragrancing, disinfecting, septic, corrosive, enzymatic, and the like. This provides the consumer with the ability to choose, for example, what fragrance she would like with her cleaning product. One limitation with current non-array-type cleaning products is that there is no degree of customizability of the overall use experience.

Figure 5:
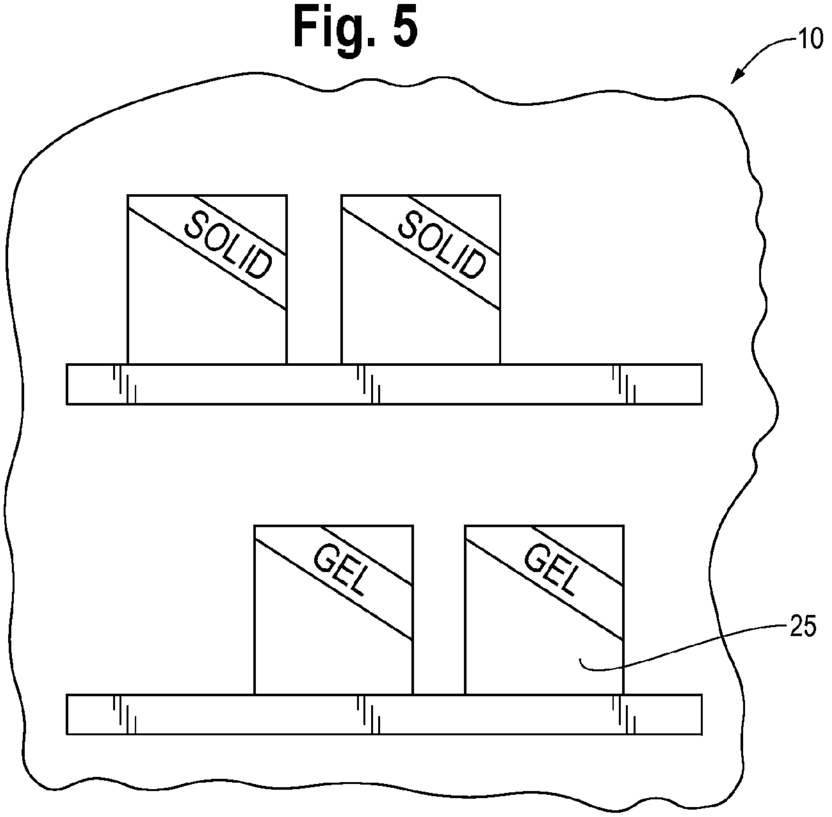
FIG. 5 shows a front view of an exemplary retail shelf unit having products displayed on the shelf unit.

In still another embodiment shown in FIG. 5, an array 10 may comprise a first product 20 and a second product 25 wherein the first and second products 20, 25 (respectively) may have different rates of dissolution with water. That is, the first product 20 may dissipate and/or dissolve faster and/or slower than the second product 25 during use. More specifically, in an exemplary embodiment, the first product 20 may dissipate from the surface of a toilet bowl (not shown) after a relatively low number of flushes, while a second product may dissipate from the surface of a toilet bowl may after a relatively high number of flushes. It is thought that such a configuration or combination provides the user the option to have a fast acting element (such as a harsh cleaner) which a user may not want to have on the surface of her toilet bowl for an extended period of time in addition to another benefit such as a fragrance, which may be provided by the second product 25.

In one embodiment, there may be one or more visual indicators or indicia on the packaging of the product and/or product itself to provide some sort of indication to the user as to the products' intended use.

Test Methods

Flush Resiliency Test

A high volume toilet bowl (American Standard Cadet Model, American Standard, Piscataway, N.J.) attached to a standard plumbing set-up is used. A water temperature of about 80° F. is used. The water has a "medium" hardness of about 120 ppm CaCu3. About 7 to about 10 g of product are metered out and the initial weight is recorded. The product is then adhered to the inner surface of the toilet bowl, about 2 inches below the upper rim. The toilet is flushed 72 times at approximately equal intervals, approximately every 96 minutes. The remaining product is removed about 30 minutes after the final flush and the weight of the remaining product is recorded. The difference between the final and initial weight is measured and recorded and then divided by the number of flushes. The resultant number is recorded as the "loss per flush". The "loss per flush" may then be divided by the initial weight. The resultant number may be reported as the "loss of initial product weight per flush."

Hardness Test

The method used to assess the hardness of a cleansing block is the "Hardness Test". The hardness measurement is in tenths of a millimeter penetration into the surface of an extrudate. Therefore, a measurement of 150 is a penetration of 150 tenths of a millimeter, or 15 millimeters. The equipment used 20 was a Precision Penetrometer (Serial #10-R-S, Manufactured by Precision Scientific Co., Chicago, Ill., USA) equipped with a large diameter cone weighing 102.4 grams with a 23D angle, and loaded with 150 grams of weight on the top of the spindle. The test method steps were: (1) Sample must be at least 'X' inches thick. (2) Place sample on the table of the instrument. (3) Both top and bottom 25 surfaces of the test sample should be relatively flat. (4) Set scale on instrument to ZERO and return cone and spindle to the upward position and lock. Clean any residual material off the cone and point before resetting for the next reading. (5) Using hand wheel, lower the complete head of the instrument with cone downward until the point of the cone touches the surface of the sample. (6) 30 Recheck the ZERO and pinch the release of the cone and spindle. (7) Hold the release handle for the count of 10 seconds and release the handle. (S) Read the dial number and record. (9) Repeat steps 4-S three times at different locations on the surface of the test sample. (10) Add the 3 recorded numbers and divide by 3 for the average. This result is the hardness of the tested sample.

With this "Hardness Test", a higher number indicates a softer product because the units of hardness are in tenths of a millimeter in penetration using the 5 test procedure delineated above. If the cleansing block is too soft (i.e., a high hardness number), then it is difficult to manufacture into shapes such as blocks because the product is too malleable. If the product is too hard (i.e., a low hardness number), then more pressure is required to push the cleansing block onto the surface, and some stickiness is lost. Typically a hardness of from about 20 to about 160 tenths of a millimeter penetration may be preferred for a cleansing block that will be applied to a dry surface. Typically a hardness of greater than 50 tenths of a millimeter penetration may be preferred for a cleansing block that will be applied to a wet surface.

Adhesion Test

The ability of a composition to adhere to an exemplary hard surface is measured as described below. A workspace is provided at a temperature of from about 86° F. to about 90° F. The relative humidity of the workspace is set to from about 40% to about 60%.

A board comprising twelve 4.25"×4.25" standard grade while glossy ceramic tiles arranged in a 3 (in the y-direction)×4 (in the x-direction) configuration (bonded and grouted) to a plexi-glass back is provided.

The board is rinsed with warm (about 75° F. to about 85° F.) tap water using a cellulose sponge. The board is then re-rinsed thoroughly with warm tap water. A non-linting cloth (ex. Kimwipe®, Kimberly Clark Worldwide, Inc., Neenah, Wis.) saturated with isopropanol is used to wipe down the entire tile board.

The board is juxtaposed to be in a horizontal position (i.e., such that the plane of the board is flat on the floor or lab bench).

Samples approximately 1.5" in diameter and weighing from about 5.5 g to about 8.0 g are provided to the surface of the board such that the bottom of the sample touches the top-most, horizontally oriented (i.e., in the x-direction), grout line of the board. Samples are spaced approximately 2" apart from each other. A permanent marker is used to draw a straight line (parallel to the x-direction) approximately 0.75" below the top-most grout line.

The board is juxtaposed to then be in the vertical position (i.e., such that the plane of the board is perpendicular with the floor or lab bench). A timer is started as the board is moved to the vertical position. The time that a sample takes for the sample to slide down the tile a distance of about 1.5 times the diameter of the sample is measured, recorded as the "sample adhesion time."

Surface Spreading Method

The "transport rate factor" is measured as described below.

A 12"×12" pane of frosted or etched glass is mounted in a flat-bottomed basin that is large enough to support the pane of glass. The basin is provided with a means for drainage such that water does not accumulate on the surface of the pane of glass as the experiment is performed at a room temperature of approximately 22° C. in ambient conditions. The pane of glass is supported on top of the bottom of the basin of water using 4"×4" ceramic tiles—one tile at each side of the bottom edge of the pane. The middle 4 inches of the pane is not touching the bottom, so that water can run down and off the glass pane. The pane of glass is juxtaposed such that pane of glass is at an angle of approximately 39° from the bottom of the basin.

The glass pane is provided with 0.5 inch measurement markers from a first edge to the opposing edge.

A glass funnel (40 mm long×15 mm ID exit, to contain >100 ml) is provided approximately 3.5" over the 9" mark of the pane of glass.

The pane of glass is cleaned with room temperature water to remove trace surface active agents. The cleaned pane of glass is rinsed until there is no observable wave spreading on the pane.

A sample of approximately 7 g. (approximately 1.5" diameter circle for gels) of composition is applied to the pane of glass at the 0 mark. Four beakers (approximately 200 mL each) of water are slowly poured over the top of the glass pane at the 9" height point and run down the pane of glass to condition the composition.

After about one minute, the funnel is then plugged and is provided with approximately 100 mL of water. An additional 100 mL of water is slowly poured onto the glass pane at approximately the 9" marker. After approximately 10 seconds, the stopper is removed and a timer is started as the water in the funnel drains onto the pane of glass.

A wave on the surface of the draining water film above the composition is observed to creep up the glass and the time for the composition to reach the 5" marker is recorded.

The test is repeated for 10 replicates and the time in seconds is averaged and reported as the "transport rate factor" (time in seconds).

While many embodiments described herein involve arrays comprising two products, any combination of two or more self-adhesive products is intended to fall within the scope of the appended claims. In some embodiments, the two or more products may be cleaning products. In other embodiments the two or more products may be directed for use on a toilet.

The exemplary embodiments herein disclosed are not intended to be exhaustive or to unnecessarily limit the scope of the claims. The exemplary embodiments were chosen and described in order to explain the principles of the present disclosure so that others skilled in the art may practice the claimed subject matter. As will be apparent to one skilled in the art, various modifications can be made within the scope of the aforesaid description. Such modifications being within the ability of one skilled in the art fall within the scope of the claims.

It is noted that terms like "specifically," preferably," "typically," "generally," and "often" are not utilized herein to limit the scope of the claims or to imply that certain features are critical, essential, or even important to the structure or function of the claims. Rather, these terms are merely intended to highlight alternative or additional features that may or may not be utilized in a particular embodiment of the disclosure. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

All documents cited in the Detailed Description are, in relevant part, incorporated herein by reference; the citation of any document is not to be construed as an admission that it is prior art with respect to this disclosure. To the extent that any meaning or definition of a term in this written document conflicts with any meaning or definition of the term in a document incorporated by reference, the meaning or definition assigned to the term in this written document shall govern.

The invention claimed is:

1. An array of self-adhesive cleaning products, the array comprising:

a) a first self-adhesive cleaning product, the first cleaning product providing a benefit selected from the group consisting of: detersive, cleansing, fragrancing, disinfecting, septic, corrosive, enzymatic; AND b) a second self-adhesive cleaning product, the second cleaning product having a surface area and providing a benefit selected from the group consisting of: detersive, cleansing, fragrancing, disinfecting, septic, corrosive, enzymatic, and the like;

c) wherein the benefit provided by the first cleaning product is different from the benefit provided by the second product;

d) wherein a first portion of the surface area is adhered to a hard surface;

e) wherein a second portion of the surface area is adhered to the first self-adhesive cleaning product, and f) wherein the first self-adhesive cleaning product and the second self-adhesive cleaning product each comprise an adhesion of at least about 5 hours.

2. The array of self-adhesive cleaning products according to claim 1, wherein the first-adhesive cleaning product and the second self-adhesive cleaning product each comprise an adhesion of from about 8 hours to about 70 hours.

3. The array of self-adhesive cleaning products according to claim 1, wherein the second self-adhesive cleaning product is adhered to the first self-adhesive cleaning product for at least the same length of time as the second product is adhered to the hard surface.

4. The array of self-adhesive cleaning products according to claim 1, wherein the first self-adhesive cleaning product is a first solid or a first gel; and wherein the second self-adhesive cleaning product is a second solid or a second gel.

5. The array of self-adhesive cleaning products according to claim 4, wherein the first gel or the second gel comprises a melt temperature of from about 50° C. to about 80° C.

6. The array of self-adhesive cleaning products according to claim 4, wherein the first gel or the second gel comprises a viscosity of from about 150,000 cps to about 400,000 cps.

7. The array of self-adhesive cleaning products according to claim 4, wherein the first solid or the second solid comprises a hardness of from about 50 to about 150 tenths of a millimeter.

8. The array of self-adhesive cleaning products according to claim 4, wherein the first gel, the second gel, the first solid, and the second solid each lose from about 0.5% to about 2% of the initial product weight per flush, according to the Flush Resiliency Test.

9. The array of self-adhesive cleaning products according to claim 4, wherein the first gel, the second gel, the first solid, and the second solid each comprise a transport rate factor of less than about 55 seconds.

10. The array of self-adhesive cleaning products according to claim 9, wherein the transport rate factor is from 0 seconds to less than about 55 seconds.

11. The array of self-adhesive cleaning products according to claim 10, wherein the transport rate factor is from about 30 seconds to less than about 55 seconds.

* * * * *

UNITED STATES PATENT AND TRADEMARK OFFICE
CERTIFICATE OF CORRECTION

PATENT NO. : 7,919,447 B1
APPLICATION NO. : 12/850553
DATED : April 5, 2011
INVENTOR(S) : Michael E. Klinkhammer, Russell B. Wortley and Michelle C. Dauchy It is certified that error appears in the above-identified patent and that said Letters Patent is hereby corrected as shown below:

Title Page, item (73);
Assignee: remove --S.C. Johnson, Inc,-- and insert --S.C. Johnson & Son, Inc.--

Signed and Sealed this
Eighteenth Day of October, 2011

David J. Kappos
*Director of the United States Patent and Trademark Office*